United States Patent
Oh et al.

(10) Patent No.: US 9,262,829 B2
(45) Date of Patent: Feb. 16, 2016

(54) METHOD AND APPARATUS FOR GENERATING A DIAGNOSTIC IMAGE BASED ON A TISSUE EMPHASIS IMAGE AND MEDICAL IMAGING SYSTEM EMPLOYING THE APPARATUS

(71) Applicant: Samsung Electronics Co., Ltd., Suwon-si (KR)

(72) Inventors: Hyun-hwa Oh, Suwon-si (KR); Sung-su Kim, Yongin-si (KR); Jae-hyun Kwon, Hwaseong-si (KR); Young-hun Sung, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 32 days.

(21) Appl. No.: 13/752,429

(22) Filed: Jan. 29, 2013

(65) Prior Publication Data
US 2013/0142412 A1 Jun. 6, 2013

Related U.S. Application Data

(63) Continuation of application No. PCT/KR2011/005636, filed on Jul. 29, 2011.

(30) Foreign Application Priority Data

Jul. 29, 2010 (KR) .................. 10-2010-0073718

(51) Int. Cl.
*G06K 9/00* (2006.01)
*G06T 7/00* (2006.01)
*A61B 6/00* (2006.01)
*G06T 5/00* (2006.01)
*G06T 5/50* (2006.01)

(52) U.S. Cl.
CPC .............. *G06T 7/0024* (2013.01); *A61B 6/4241* (2013.01); *A61B 6/482* (2013.01); *A61B 6/5235* (2013.01); *G06T 5/003* (2013.01); *G06T 5/50* (2013.01); *G06T 2207/10116* (2013.01); *G06T 2207/20016* (2013.01); *G06T 2207/20221* (2013.01)

(58) Field of Classification Search
None
See application file for complete search history.

(56) References Cited

U.S. PATENT DOCUMENTS

| 4,816,681 A | 3/1989 | Shimura |
| 6,614,873 B1 | 9/2003 | Taylor et al. |

(Continued)

FOREIGN PATENT DOCUMENTS

| CN | 1504931 A | 6/2004 |
| CN | 101175440 A | 5/2008 |

(Continued)

OTHER PUBLICATIONS

Japanese Office Action mailed Apr. 22, 2014 in Japanese Application No. 2013-521721 (5 pages, in Japanese, with English translation of the substantive portion).

(Continued)

*Primary Examiner* — Jason Heidemann
(74) *Attorney, Agent, or Firm* — NSIP Law

(57) ABSTRACT

A method of processing an image is provided. The method includes generating a tissue emphasis image by emphasizing a predetermined tissue of at least two radiation images of different energy bands, and generating a diagnostic image by combining at least one of the at least two radiation images of different energy bands and the tissue emphasis image.

17 Claims, 8 Drawing Sheets

(56) References Cited

U.S. PATENT DOCUMENTS

| | | |
|---|---|---|
| 7,796,795 B2 | 9/2010 | Uppaluri et al. |
| 7,869,560 B2 | 1/2011 | Imai |
| 7,876,874 B2 | 1/2011 | Goto et al. |
| 8,041,096 B2 | 10/2011 | Bernhardt et al. |
| 2001/0053240 A1 | 12/2001 | Oosawa |
| 2003/0147497 A1 | 8/2003 | Avinash |
| 2003/0160800 A1* | 8/2003 | Vuylsteke ............ 345/589 |
| 2003/0161519 A1* | 8/2003 | Vuylsteke ............ 382/128 |
| 2009/0022263 A1 | 1/2009 | Imai |
| 2009/0122953 A1* | 5/2009 | Imai ................... 378/5 |
| 2009/0147919 A1* | 6/2009 | Goto et al. ............ 378/86 |
| 2010/0142790 A1* | 6/2010 | Chang ................ 382/132 |
| 2010/0266188 A1* | 10/2010 | Burns et al. .......... 382/132 |
| 2010/0266189 A1* | 10/2010 | Knapp et al. ......... 382/132 |
| 2011/0002524 A1* | 1/2011 | Sun ................... 382/132 |
| 2012/0014583 A1* | 1/2012 | Sun ................... 382/132 |
| 2012/0063662 A1* | 3/2012 | Kwon et al. .......... 382/132 |

FOREIGN PATENT DOCUMENTS

| | | |
|---|---|---|
| CN | 101433464 A | 5/2008 |
| JP | 61-85929 A | 5/1986 |
| JP | 3-132272 A | 6/1991 |
| JP | 5-45470 A | 2/1993 |
| JP | 8-336517 A | 12/1996 |
| JP | 2002-530171 A | 9/2002 |
| JP | 2006-320464 | 11/2006 |
| JP | 2008-86543 A | 4/2008 |
| JP | 2008-272476 A | 11/2008 |
| JP | 2009-22450 A | 2/2009 |
| JP | 2009-082174 | 4/2009 |
| KR | 10-2001-0087543 A | 9/2001 |
| KR | 10-2004-0047561 | 6/2004 |

OTHER PUBLICATIONS

Korean Office Action mailed Apr. 29, 2014 in Korean Application No. 10-2010-0073718 (7 pages, in Japanese, with English translation of the substantive portion).

Chinese Office Action issued Jul. 29, 2014 in corresponding Chinese Application No. 201180037295.4 (19 pages, with English translation).

Korean Notice of Allowance issued on Oct. 30, 2014 in corresponding Korean Application No. 10-2010-0073718 (3 pages, with English translation).

Japanese Office Action issued on Nov. 4, 2014 in corresponding Japanese Application No. 2013-521721 (4 pages, with English translation).

Japanese Office Action issued on Jul. 7, 2015 in counterpart Japanese Application No. 2013-521721 (5 pages with English translation).

* cited by examiner

METHOD AND APPARATUS FOR GENERATING A DIAGNOSTIC IMAGE BASED ON A TISSUE EMPHASIS IMAGE AND MEDICAL IMAGING SYSTEM EMPLOYING THE APPARATUS

CROSS-REFERENCE TO RELATED APPLICATION(S)

This application is a continuation of International Patent Application No. PCT/KR2011/005636 filed on Jul. 29, 2011, which claims the benefit of Korean Patent Application No. 10-2010-0073718, filed on Jul. 29, 2010, in the Korean Intellectual Property Office, the entire disclosures of which are incorporated herein by reference for all purposes.

FIELD

The following description relates to a method and apparatus for processing an image, and a medical imaging system employing the apparatus.

DESCRIPTION OF RELATED ART

A medical imaging system that uses radiation may obtain a radiation image by irradiating X-rays onto a subject, such as a human body. The amount of X-rays absorbed by the subject depends on a type and a density of the particular portion of the subject and/or on an X-ray energy band.

For example, an X-ray absorption coefficient of bone is much higher than that of soft tissue. In this example, because a contrast between the bone and the soft tissue is high in the radiation image, the soft tissue and the bone of the radiation image may be clearly identified. However, different tissues that are included within the soft tissue have similar X-ray absorption coefficients. Accordingly, the tissues tend to have similar intensities in the radiation image, which makes it difficult to identify different soft tissue due to a low contrast between soft tissues.

SUMMARY

In an aspect, there is provided an image processing method including generating a tissue emphasis image by emphasizing a predetermined tissue of at least two radiation images of different energy bands, and generating a diagnostic image by combining at least one of the at least two radiation images of different energy bands and the tissue emphasis image.

The generating of the tissue emphasis image may comprise generating a difference image by applying a variable weight to the at least two radiation images of different energy bands, analyzing transform coefficients by transforming the difference image into a frequency domain, repeatedly performing the generating of the difference image and the analyzing of the transform coefficients by changing the variable weight, and setting the variable weight corresponding to a point having a maximum change in a sum of high frequency coefficients of the difference image as an optimal weight, and outputting the difference image corresponding to the set optimal weight as the tissue emphasis image.

The image processing method may further comprise correcting the at least two radiation images of different energy bands and generating the tissue emphasis image based on the corrected at least two radiation images.

The image processing method may further comprise pre-processing the corrected at least two radiation images, and generating the diagnostic image based on the pre-processed at least two radiation images.

In an aspect, there is provided an image processing apparatus including a tissue emphasis image generating unit configured to generate a tissue emphasis image by emphasizing a predetermined tissue of at least two radiation images of different energy bands, and a combining unit configured to generate a diagnostic image by combining at least one of the at least two radiation images of different energy bands and the tissue emphasis image.

The tissue emphasis image generating unit may be configured to generate a difference image by applying a variable weight to the at least two radiation images of different energy bands, analyze transform coefficients by transforming the difference image into a frequency domain, perform the generating of the difference image and the analyzing of the transform coefficients repeatedly by changing the variable weight, set the variable weight corresponding to a point having a maximum change in a sum of high frequency coefficients of the difference image corresponding to the changed variable weight as an optimal weight, and outputs the difference image corresponding to the set optimal weight as the tissue emphasis image.

The image processing apparatus may further comprise a correcting unit configured to correct the at least two radiation images of different energy bands and to provide the corrected at least two radiation images to the tissue emphasis image generating unit.

The image processing apparatus may further comprise a pre-pre-processing unit configured to pre-process the corrected at least two radiation images, and to provide the pre-processed at least two radiation images to the tissue emphasis image generating unit.

In an aspect, there is provided a medical imaging system including an image processing apparatus configured to generate a tissue emphasis image by emphasizing a predetermined tissue of at least two radiation images of different energy bands, and to generate a diagnostic image by combining at least one of the at least two radiation images of different energy bands and the tissue emphasis image.

The medical imaging system may further comprise a radiation image obtaining unit configured to irradiate radiation having at least two different energy bands onto a subject and to obtain the at least two radiation images of the subject.

The medical imaging system may further comprise a storage unit configured to store the generated diagnostic image and/or to store diagnosis information obtained from the generated diagnostic image in correspondence to the diagnostic image.

The medical imaging system may further comprise a communication unit configured to transmit the generated diagnostic image or transmitting diagnosis information obtained from the generated diagnostic image in correspondence to the diagnostic image.

In an aspect, there is provided an image processing device including a receiver configured to receive a plurality of radiation images of a subject, the plurality of radiation images being obtained using different energy bands, and an image generator configured to generate an image of interest in which one or more tissues of non-interest are removed based on absorption coefficients of the one or more tissues of non-interest and the different energy bands.

The plurality of radiation images may be obtained using a plurality of different radiation sources or by a detector configured to identify the different energy bands.

The image processing device may further comprise a combiner configured to combine the plurality of radiation images and the image of interest to generate a diagnostic image in which a tissue of interest is emphasized.

Other features and aspects may be apparent from the following detailed description, the drawings, and the claims.

Figure 1:
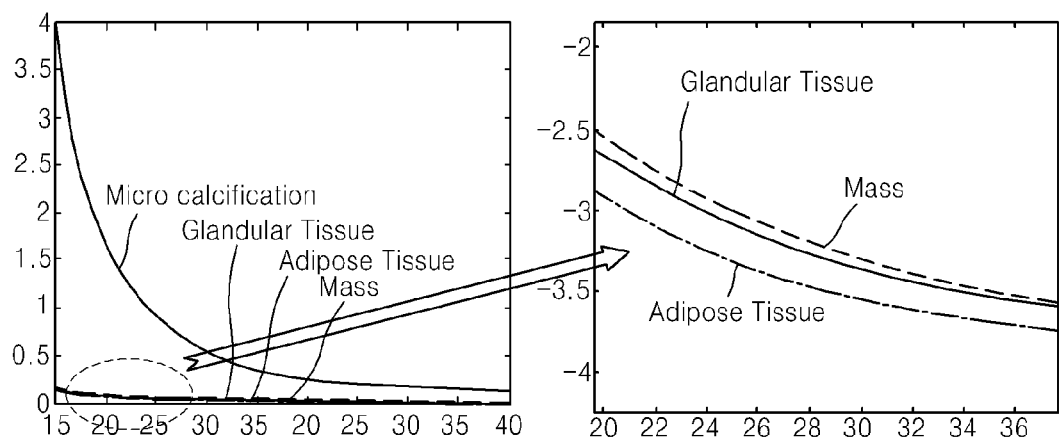
FIG. 1 is an example of a graph illustrating an absorption coefficient of various materials of a breast tissue with respect to X-ray energy bands.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 is a graph that illustrates an example of an absorption coefficient of various materials of a breast tissue for with respect to X-ray energy bands. Referring to FIG. 1, a glandular tissue, an Adipose tissue, and a mass tissue correspond to soft tissues. In this example, the soft tissues have relatively low absorption coefficients. Further, the absorption coefficients between the soft tissues, i.e. the glandular tissue, the Adipose tissue, and the mass tissue make little difference. Micro calcifications are harder masses that may form in the breast tissue. As can be seen in the graph of FIG. 1, the harder micro calcification tissue has a relatively greater absorption coefficient than the soft tissues.

Figure 2:
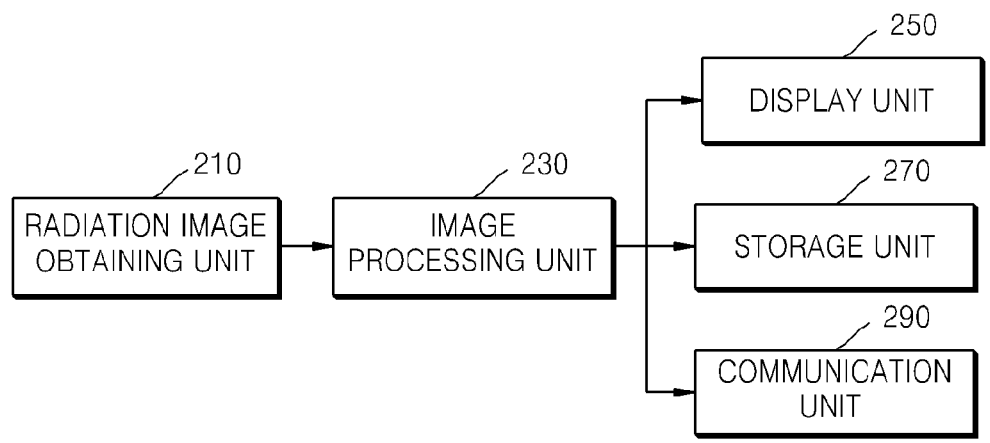
FIG. 2 is a diagram illustrating an example of a medical imaging system.

FIG. 2 illustrates an example of a medical imaging system. Referring to FIG. 2, the medical imaging system includes a radiation image obtaining unit 210, an image processing unit 230, a display unit 250, a storage unit 270, and a communication unit 290. As an example, the medical imaging system may be implemented as the image processing unit 230 only. That is, the radiation image obtaining unit 210, the display unit 250, the storage unit 270, and the communication unit 290 are optionally included in the example medical imaging system of FIG. 2. For example, the image processing unit 230 may be implemented as at least one processor.

The radiation image obtaining unit 210 may irradiate radiation having at least two different energy bands onto a subject and may obtain at least two radiation images of the subject. As another example, the radiation image obtaining unit 210 may irradiate radiation having a wideband spectrum onto the subject, and may obtain two or more radiation images using a detector capable of identifying energy. If radiation irradiated onto the same tissue of the subject, e.g. X-ray energy band, differs, the corresponding tissue may have different levels of absorption. For example, the radiation image obtaining unit 210 may obtain a plurality of radiation images reflecting the absorption characteristics for energy bands, by irradiating X-ray having two or more energy bands onto corresponding tissues or by using the detector capable of identifying energy.

The image processing unit 230 may generate a tissue emphasis image by emphasizing anatomic information of tissues of the radiation images for energy bands provided by the radiation image obtaining unit 210, and may generate a radiation diagnostic image using the radiation images for energy bands and the tissue emphasis image. For example, the image processing unit 230 may generate the tissue emphasis image in which anatomic structures of tissues of human organs are distinguished using different absorption characteristics of the tissues for energy bands. Meanwhile, the radiation diagnostic image may be generated by combining or overlapping at least one of the radiation images for energy bands and the tissue emphasis image. The image processing unit 230 may also have an image reading function, and thus may generate diagnosis information from the radiation diagnostic image.

The display unit 250 may include a monitor, and may display the radiation diagnostic image generated by the image processing unit 230, and may display the diagnosis information obtained by the image processing unit 230 together with the radiation diagnostic image.

The storage unit 270 may include a memory device, and may store the radiation diagnostic image generated by the image processing unit 230, and may store the diagnosis information obtained by the image processing unit 230, in correspondence with the radiation diagnostic image.

The communication unit 290 may transmit the diagnostic image generated by the image processing unit 230, or the radiation diagnostic image combined with the diagnosis information to another medical imaging system. The communication unit 290 may use wireless and/or wired communication. For example, the communication unit 290 may transmit data to another medical imaging system located at a remote place or a specialist such as a doctor at a hospital, and may receive the multi-energy radiation image provided from the other medical imaging system. Accordingly, the communication unit 290 may input the image to the image processing unit 230. That is, the communication unit 290 may transmit by a wired or wireless network the radiation diagnostic image, or the radiation diagnostic image combined with the diagnosis information to another medical imaging system or a specialist who has transmitted the multi-energy radiation image.

In this example, the storage unit 270 and the communication unit 290 may be integrated into a picture archiving communication system (PACS) by adding image reading and searching functions. In this example, the medical imaging system of FIG. 2 may include image diagnosis systems that use, for example, X-rays. For example, the medical imaging system may be a mammography image diagnosis system used to identify lesions in breast tissue including soft tissue, but not hard tissue such as bone, of a human body.

Figure 3A:
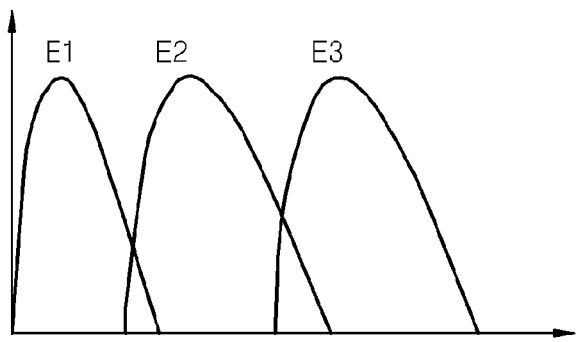
FIGS. 3A and 3B are diagrams illustrating examples of obtaining a multi-energy radiation image.
Figure 3B:
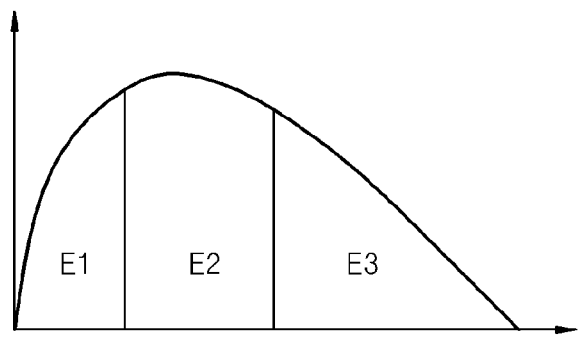

FIGS. 3A and 3B illustrate examples of obtaining a multi-energy radiation image. Referring to FIGS. 3A and 3B, the multi-energy radiation image may be obtained using a plurality of radiation sources, for example, an X-ray source, or may be obtained using a detector for identifying different energy bands when an X-ray source emits wideband spectrum X-ray. In this example, the X-ray sources may have different energy bands emitted according to anode materials of the X-ray source. Thus, filters may be combined with X-ray source having different energy bands like E1, E2, and E3 of FIG. 3A and may be sequentially irradiated to tissues, thereby obtaining a plurality of radiation images for energy bands. Referring to FIG. 3B, the detector may obtain a plurality of radiation images for energy bands by dividing an X-ray source having a wideband spectrum like tungsten into a plurality of energy bins. For example, a photo coefficient detector may be used to calculate the number of photons incident thereto for X-ray energy bands and may generate an image from a calculation result. In this example, the horizontal and vertical axes of the graphs of FIGS. 3A and 3B indicate photon energy and intensity, respectively.

Figure 4:
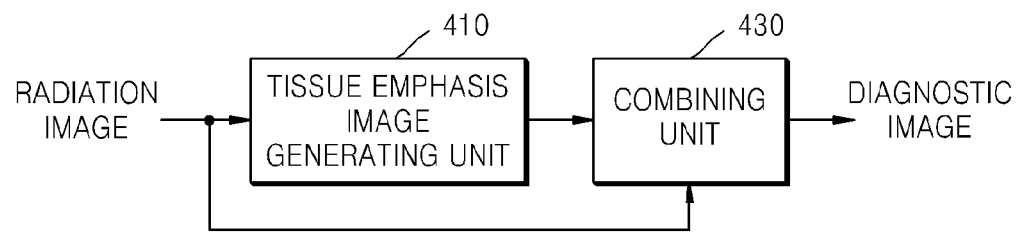
FIG. 4 is a diagram illustrating an example of an image processing apparatus.

FIG. 4 illustrates an example of an image processing apparatus. The image processing apparatus includes a tissue emphasis image generating unit 410 and a combining unit 430. In this example, the tissue emphasis image generating unit 410 and the combining unit 430 may be implemented as at least one processor.

Referring to FIG. 4, the tissue emphasis image generating unit 410 may generate a tissue emphasis image by emphasizing previously set tissues for a plurality of radiation images for energy bands. In this example, the emphasizing of the previously set tissues may include a removal of a tissue of non-interest. For example, the emphasizing may set an absorption coefficient ratio of tissue A as a weight because an X-ray of two different energy bands for the same tissue A may have different absorption coefficients. That is, the tissue emphasis image generating unit 410 may obtain radiation images for energy bands and may generate an image in which tissue A is removed, i.e. the tissue emphasis image, by processing weighted subtraction on the radiation images for energy bands.

In this example, tissue A may be removed such that a final radiation image may include tissues other than tissue A, and thus a contrast between the tissues other than tissue A may increase. For example, the tissue of non-interest areas other than a tissue of interest may be removed from a breast tissue image, thereby generating a diagnosis image to more easily identify lesions. For example, an adipose tissue that is most distributed in the breast tissue may be removed by using absorption coefficients for energy bands. As a result, the diagnostic image having an increased contrast of the tissue of interest other than the adipose tissue may be obtained. As another example, a fibroglandular tissue of the breast tissue may be removed in the same manner as in the adipose tissue, thereby obtaining a diagnostic image from which the fibroglandular tissue is removed. Accordingly, the tissue of non-interest areas may be removed from the radiation image, thereby generating the diagnostic image in which a tissue important in identifying lesions is emphasized.

The combining unit 430 may combine the radiation image having different energy bands and the tissue emphasis image provided by the tissue emphasis image generating unit 410 and may generate a diagnostic image having a high contrast between different soft tissues.

Figure 5:
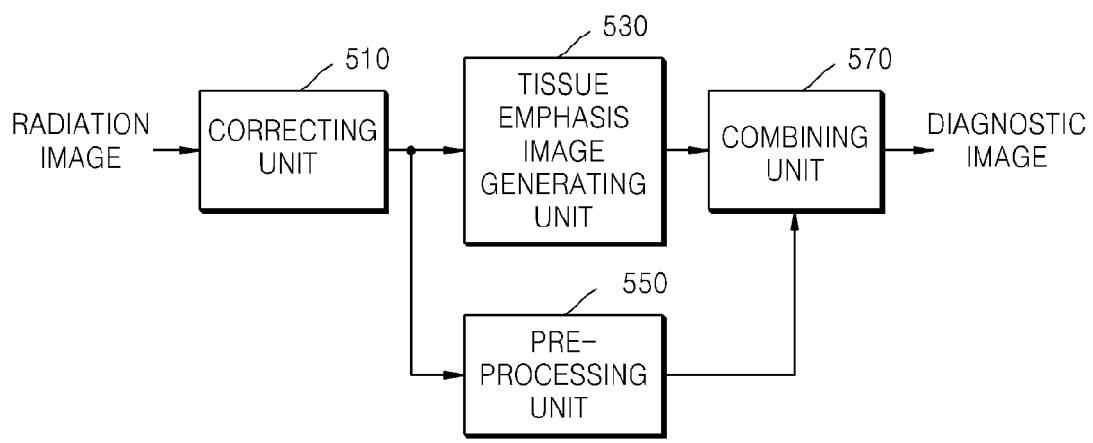
FIG. 5 is a diagram illustrating another example of an image processing apparatus.

FIG. 5 illustrates another example of an image processing apparatus. The image processing apparatus includes a correcting unit 510, a tissue emphasis image generating unit 530, a pre-processing unit 550, and a combining unit 570. In this example, the correcting unit 510, the tissue emphasis image generating unit 530, the pre-processing unit 550, and the combining unit 570 may be implemented as at least one processor. In this example, the tissue emphasis image generating unit 530 and the combining unit 570 may perform the same or similar function as the tissue emphasis image generating unit 410 and the combining unit 430 of FIG. 4, respectively.

Referring to FIG. 5, the correcting unit 510 may correct a signal distortion of a multi-energy radiation image caused by the non-linearity characteristics of a detector according to X-ray energy bands. For example, the correcting unit 510 may use a variety of well-known calibration methods. The corrected multi-energy radiation image may be provided to the tissue emphasis image generating unit 530.

The pre-processing unit 550 may reduce various noise components, for example, noise of an X-ray source, noise of the detector, scattering noise, etc. of the multi-energy radiation image. The pre-processing unit 550 may enhance a contrast of the multi-energy radiation image. For example, the pre-processing unit 550 may use a variety of well-known noise reduction methods or an image based contrast enhancement method.

The combining unit 570 may combine a plurality of radiation images that have emphasized tissues provided by the tissue emphasis image generating unit 530 and a plurality of radiation images pre-processed by the pre-processing unit 550 for spatial frequency bands of images, and may generate a diagnostic image that includes general anatomic structure information and emphasizes tissues of interest important in identifying lesions.

Figure 6:
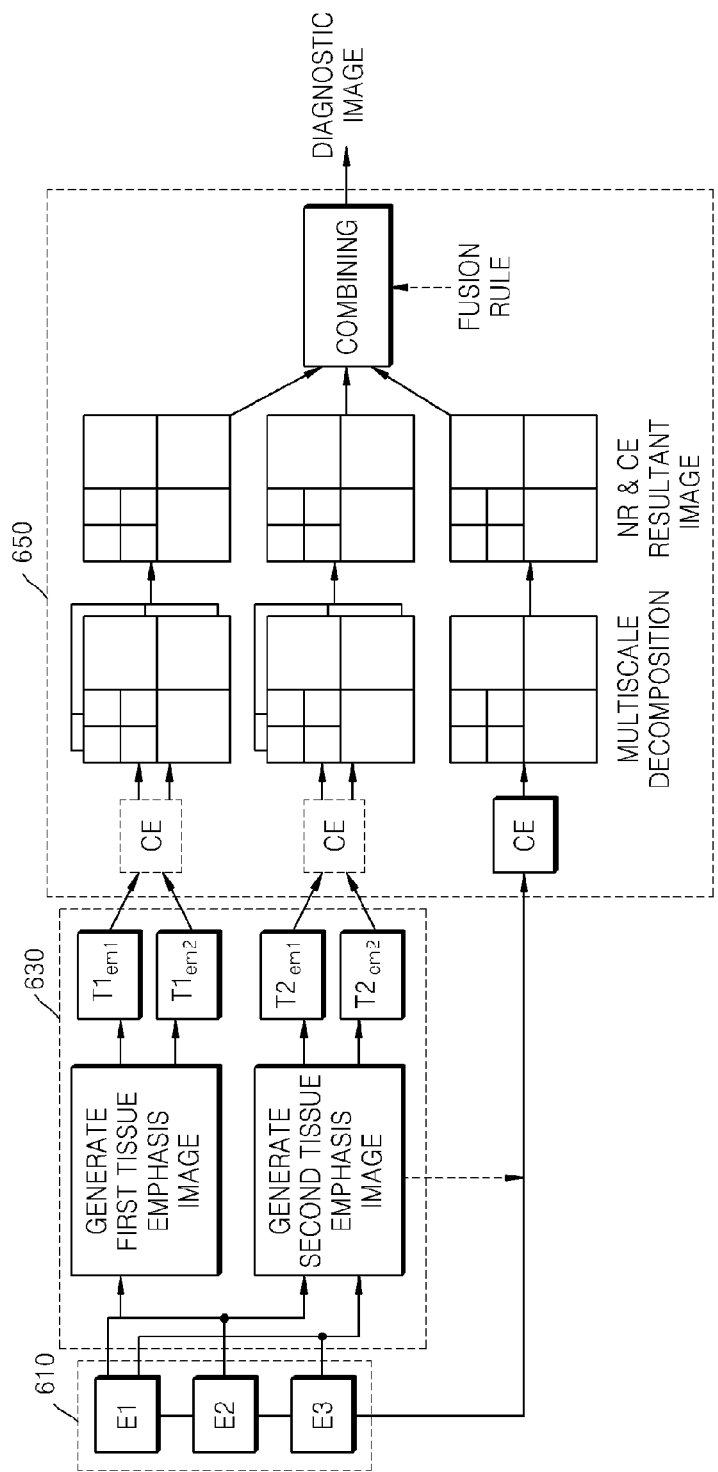
FIG. 6 is a diagram illustrating another example of an image processing apparatus.

FIG. 6 illustrates another example of an image processing apparatus. Referring to FIG. 6, the image processing apparatus includes a tissue emphasis image generating unit 630 and a high resolution diagnostic image generating unit 650. As an example, the tissue emphasis image generating unit 630 may generate a first tissue emphasis image and a second tissue emphasis image for radiation images 610 for three energy bands E1, E2, and E3.

The high resolution diagnostic image generating unit 650 may perform contrast enhancement (CE) processing on the radiation images 610 for the three energy bands E1, E2, and E3. The high resolution diagnostic image generating unit 650 may also perform CE processing on the first tissue emphasis image and the second tissue emphasis image generated by the tissue emphasis image generating unit 630. That is, the CE processing may be optionally performed. Frequency domain transform processing and multi-scale decomposition processing may be performed on the radiation images 610 and the first tissue emphasis image and the second tissue emphasis image on which CE processing has been or has not been performed. For example, frequency domain transform processing and multi-scale decomposition processing may allow each of the radiation images 610 and the first tissue emphasis image and the second tissue emphasis image to be decomposed as a low frequency band such as an approximation band, and a high frequency band, i.e. a detail band. In this example, multi-scale decomposition processing may use contourlet transform, curvelet transform, and the like, in view of various edge directivities and simple wavelet transform as well.

At least two tissue emphasis images that emphasize the same tissue may be generated from the radiation images 610 for three energy bands E1, E2, and E3. In this example, the high resolution diagnostic image generating unit 650 may perform noise reduction (NR) processing on the low frequency bands and the high frequency bands generated as a result of performing multi-scale decomposition processing on the first tissue emphasis image and the second tissue emphasis image. For example, spatial filters for frequency bands of the first tissue emphasis image and the second tissue emphasis image may be used to perform spatial NR processing. Also, noise included in the first tissue emphasis image and the second tissue emphasis image may be reduced by means of NR processing in which the first tissue emphasis image and the second tissue emphasis image are referred to each other.

The high resolution diagnostic image generating unit 650 may also perform CE processing on the low frequency bands and the high frequency bands generated as a result of performing multi-scale decomposition processing on the first tissue emphasis image and the second tissue emphasis image. In this example, CE processing may be optionally performed. For example, the high resolution diagnostic image generating unit 650 may perform CE processing after performing NR processing, or may perform NR processing after performing CE processing.

The high resolution diagnostic image generating unit 650 may combine the low frequency bands and the high frequency bands on which NR processing and CE processing have been performed or the low frequency bands and the high frequency bands on which NR processing has been performed by applying a predetermined fusion rule, and may generate a sheet of high resolution diagnostic image.

Figure 7:
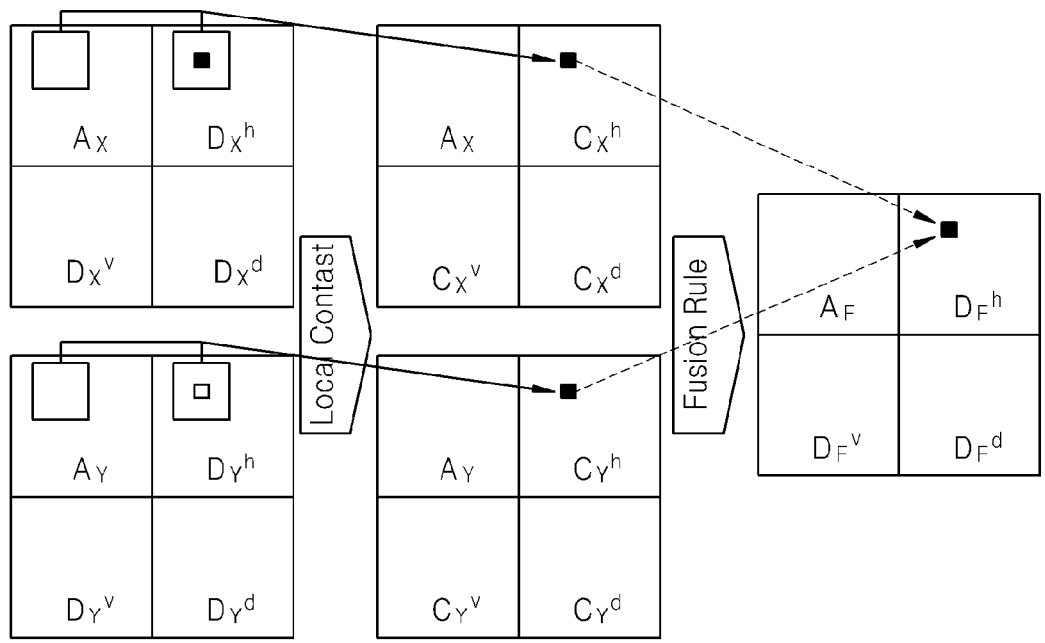
FIG. 7 is a diagram illustrating an example of combining two images by applying a fusion rule.

FIG. 7 illustrates an example of combining two images X and Y on which multi-scale decomposition has been performed by applying a fusion rule. In this example, a contrast based combining method may be applied in order to maintain a maximum contrast of images to be combined. Referring to FIG. 7, a local contrast may be computed using coefficient values of low frequency bands and high frequency bands of the two images X and Y which are to be combined, and the two images X and Y may be combined based on the local contrast. In this example, the local contrast $C_l^k$ of a band k of a level l on which multi-scale decomposition has been performed may be expressed according to Equation 1, $$C_l^k = \max(D_l^k)/M_l \qquad \text{<Equation 1>}$$

wherein, $D_l^k$ denotes the band k (k=h, v, d) in a detail band of the level l on which multi-scale decomposition is performed, and $M_l$ denotes an average of coefficients of a predetermined local region in an approximation band of the level l on which multi-scale decomposition has been performed.

The combination in the approximation band may be expressed according to Equation 2, $$A_{L,F}(i,j) = w_X A_{L,X}(i,j) + w_Y A_{L,Y}(i,j) \qquad \text{<Equation 2>}$$

wherein, $A_{L,F}(i,j)$ denotes an approximation band coefficient value that is approximately combined at a coordinate of (i,j) in the level l on which multi-scale decomposition has been performed, $w_X$, $w_Y$ denote weights with respect to absorption coefficients for energy bands applied to the images X and Y, and $A_{L,X}(i,j)$, $A_{L,Y}(i,j)$ denote approximation band coefficient values at the coordinate of (i,j) in the level l of the images X and Y to be combined on which multi-scale decomposition has been performed.

The combination in the detail band maybe expressed according to Equation 3, $$D_{l,F}^k(i,j) = D_{l,X}^k(i,j), \text{ if } |C_{l,X}^k| > |C_{l,Y}^k| \qquad \text{<Equation 3>}$$
$$= D_{l,Y}^k(i,j), \text{ otherwise}$$

wherein, $D_{l,X}^k(i,j)$, $D_{l,Y}^k(i,j)$ denote coefficients in the detail band for the coordinate (i,j) in a band k of a level l at which the images X and y have been transformed to a frequency domain, and $D_{l,F}^k(i,j)$ denotes a combination result of the detail band for the coordinate (i,j) in the band k in the level l at which the images X and y have been transformed to a frequency domain. $C_{l,X}^k$, $C_{l,Y}^k$ denote contrasts in the local region (i,j) of the band k in the level l at which the images X and y have been transformed to a frequency domain.

Accordingly, a sheet of combined high resolution diagnostic images may be generated by performing inverse transform on results of combination for bands.

Figure 8:
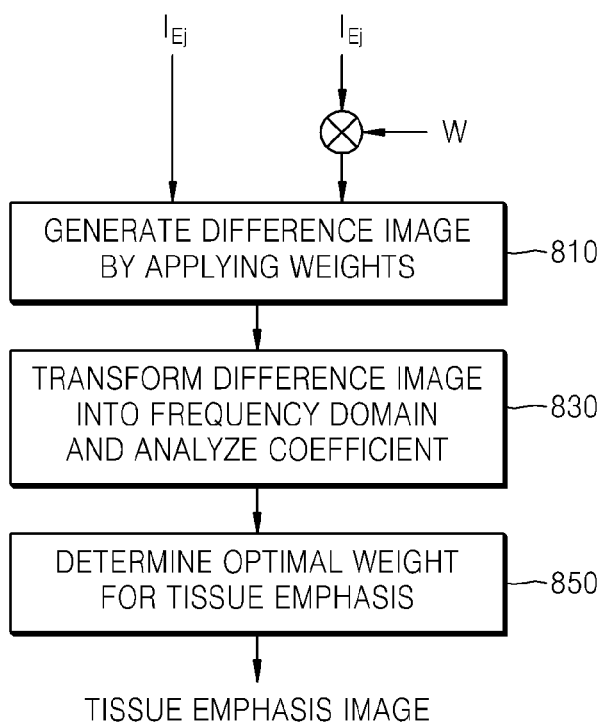
FIG. 8 is a diagram illustrating an example of a method of generating a tissue emphasis image.

FIG. 8 illustrates an example of a method of generating a tissue emphasis image. The method of generating the tissue emphasis image of FIG. 8 may be performed by at least one processor.

According to various aspects, reduction processing may be performed on a monochromatic X-ray image of two different energy bands using an X-ray absorption coefficient ratio of a specific tissue in two different energy bands as a weight, thereby obtaining an image from which the specific tissue is removed. In this example, a contrast of a tissue other than the specific tissue may relatively increase, which provides an emphasis effect. Meanwhile, the absorption characteristics for various energy bands may be reflected on a polychromatic X-ray image. Thus, it may be desirable to determine an optimal weight in order to generate a tissue emphasis image.

Referring to FIG. 8, in 810, a difference image between an image obtained by applying variable weights W to a radiation image $I_{Ej}$ of two energy bands and the radiation image $I_{Ej}$ of two energy bands is generated.

In 830, the difference image generated in 810 is transformed into a frequency domain, and transform coefficients are analyzed. For example, a transform method may use discrete cosine transform (DCT) but is not limited thereto. Operations 810 and 830 may be repeatedly performed by varying the variable weights W.

In 850, an optical weight is determined among the variable weights W in response to an analysis result obtained in 830. That is, the difference image from which a specific tissue has been removed may be generated by varying the variable weights W. In this example, detail information of the image may change in response to the variable weights W. For example, if the variable weight W corresponding to a point having a maximum change in a sum of high frequency coefficients of the difference image is selected, the difference image generated from the selected variable weight W may become a tissue emphasis image from which a specific tissue has been removed.

Figure 9:
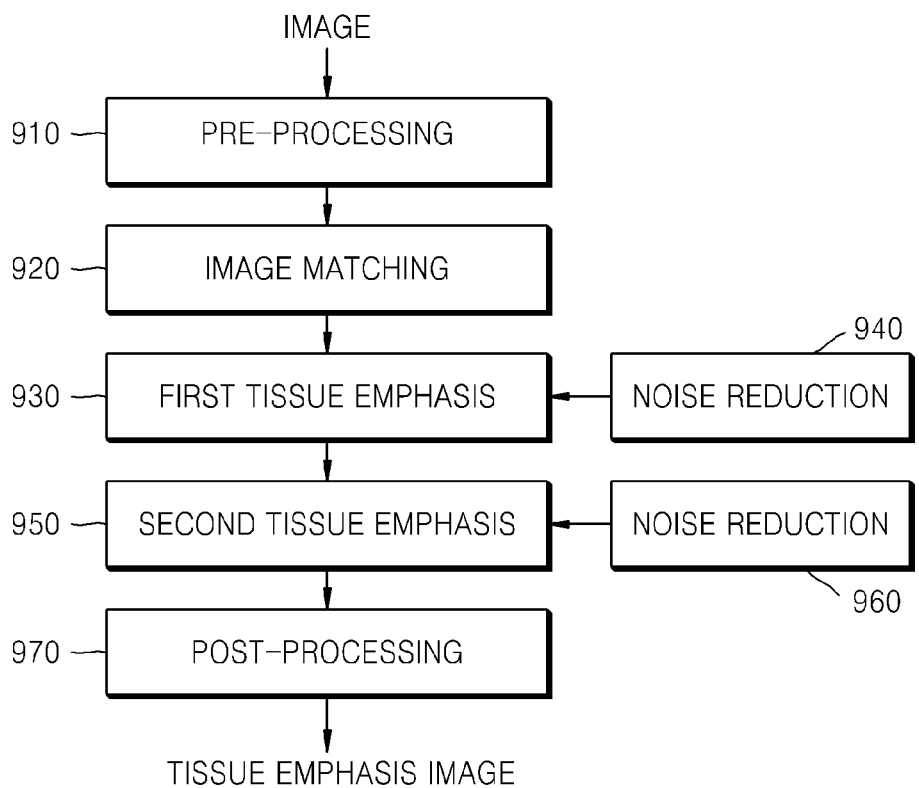
FIG. 9 is a diagram illustrating another example of a method of generating a tissue emphasis image.

FIG. 9 illustrates another example of a method of generating a tissue emphasis image.

Referring to FIG. 9, in 910, pre-processing is performed on a multi-energy band radiation image. In this example, pre-processing may reduce various noise components, such as noise of an X-ray source, noise of a detector, scattering noise, etc. of the multi-energy radiation image. The pre-processing may also enhance a contrast of the multi-energy radiation image. For example, a variety of well-known noise reduction methods or an image based contrast enhancement method may be used. The pre-processing may be optionally performed.

In 920, image matching is performed on the multi-energy radiation image on which the pre-processing has been performed.

In 930, a first tissue emphasis image is generated for the multi-energy radiation image on which image matching has been performed. Meanwhile, in 940, noise reduction processing is performed on the first tissue emphasis image generated in 930.

In 950, a second tissue emphasis image is generated for the first tissue emphasis image. Meanwhile, in 960, noise reduction processing is performed on the second tissue emphasis image generated in 950.

In 970, post-processing is performed on the second tissue emphasis image. In this example, post-processing may include image based contrast enhancement processing, but is not limited thereto.

In this example, tissue emphasis images may be generated, thereby solving a reduction of a dynamic range of a soft tissue image due to a phenomenon of hiding a soft tissue, and thus a contrast of a soft tissue image of interest may be enhanced.

Figure 10:
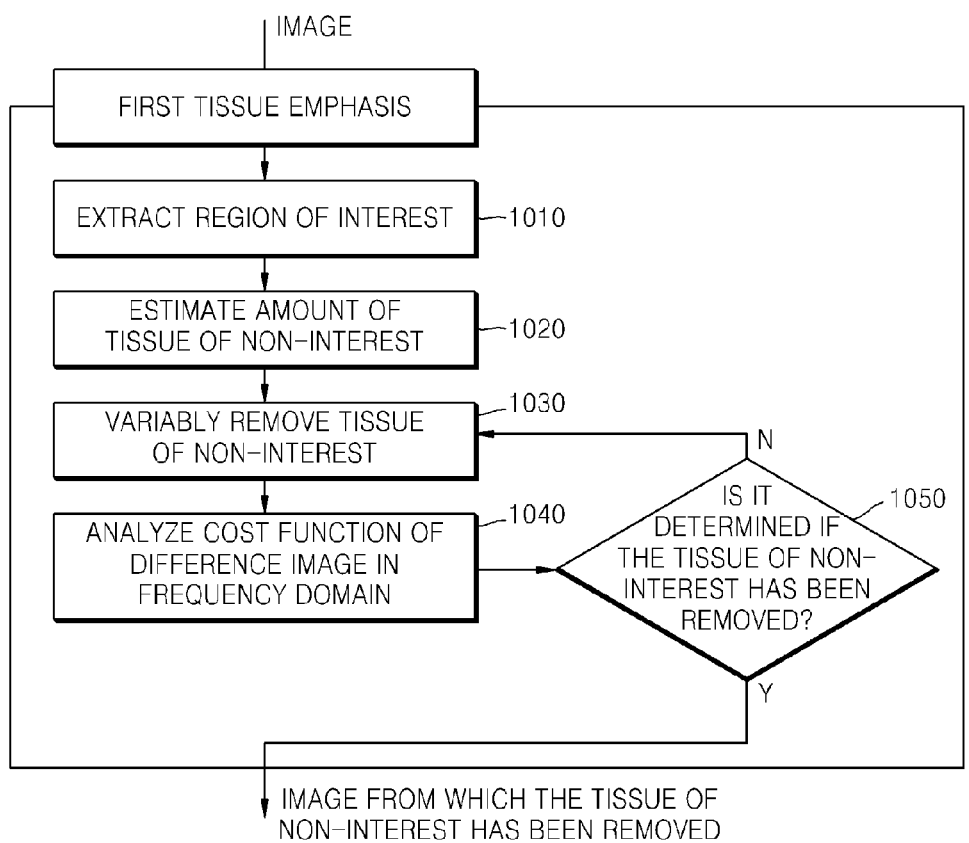
FIG. 10 is a diagram illustrating an example of a method of generating a first step tissue emphasis image.

FIG. 10 illustrates an example of a method of generating a first tissue emphasis image.

Referring to FIG. 10, in 1010, a region of interest is extracted from radiation images for energy bands. For example, a region of interest including an adipose tissue and a fibro-glandular tissue may be extracted from a line profile for radiation images for energy bands with respect to a subject, for example, a breast tissue.

In 1020, an amount of tissues of non-interest is estimated with respect to the extracted region of interest. In 1030, a tissue of non-interest is variably removed. For example, the amount of tissues of non-interest may be estimated by selecting an expectation value based on a method of using an anatomic tissue structure of breasts. The tissue of non-interest, for example, the adipose tissue, may be suppressed by estimating an optimal offset that minimizes or otherwise reduces a structure loss based on the radiation images for energy bands.

In 1040, a difference image between the radiation images for energy bands from which the tissue of non-interest has been variably removed and the radiation images for energy bands is generated, the difference image is transformed into a frequency domain, and a cost function may be analyzed.

In 1050, whether the tissue of non-interest has been removed is determined in response to an analysis result of the cost function, and, if it is determined that the tissue of non-interest has been removed, the first tissue emphasis image from which the tissue of non-interest has been removed may be generated.

Figure 11:
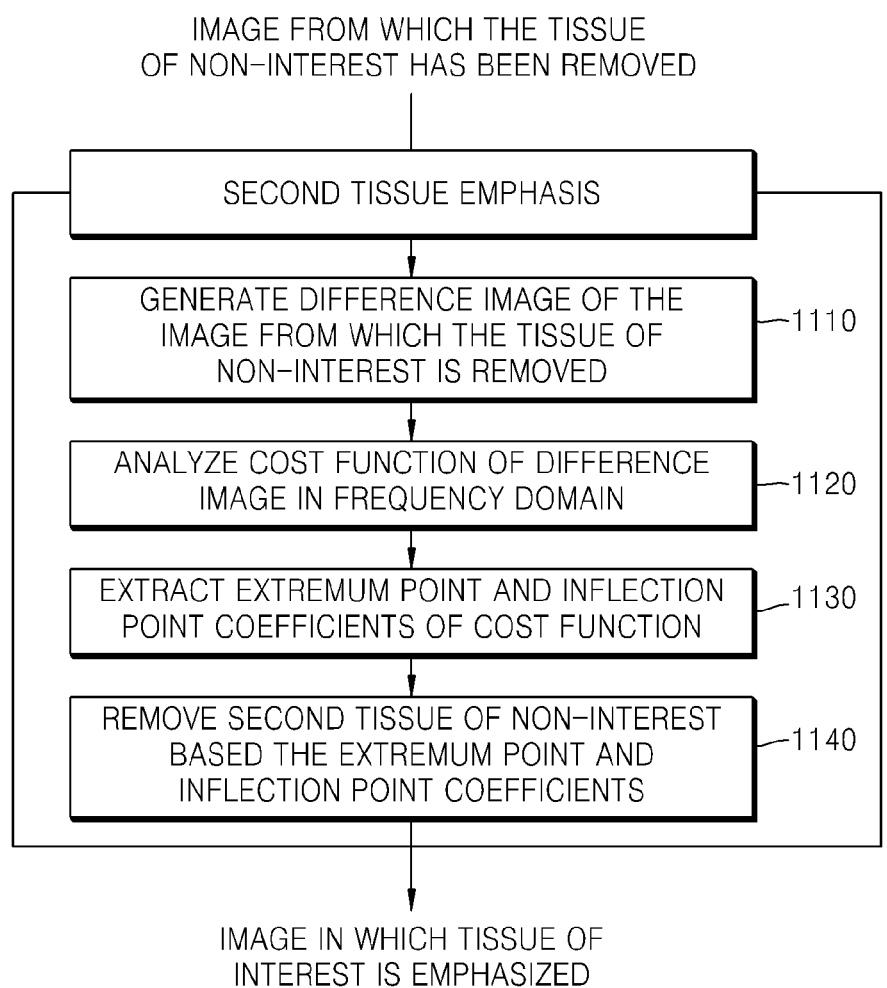
FIG. 11 is a diagram illustrating an example of a method of generating a second step tissue emphasis image.

FIG. 11 illustrates an example of a method of generating a second tissue emphasis image.

Referring to FIG. 11, in 1110, a difference image of the first tissue emphasis image is generated.

In 1120, the difference image is transformed into a frequency domain, and a cost function is analyzed. In 1130, extremum point and inflection point coefficients are extracted from the cost function.

In 1140, the second tissue emphasis image is generated by removing the tissue of non-interest from the first tissue emphasis image based on the extremum point and inflection point coefficients of the cost function. In this example, the extremum point and inflection point coefficients of the cost function may be used to identify soft tissues having a relatively similar mass attenuation curve.

According to various aspects, a diagnostic image having a high resolution may be obtained by emphasizing a predetermined tissue of a multi-energy radiation image, thereby increasing accuracy of a diagnosis. Accordingly, radiation image diagnostic devices that are used to display soft tissues hidden by bones or to increase distinctions between soft tissues may provide a clear tissue distinction, thereby increasing identification of lesions.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, maybe distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An image processing method comprising:
generating a tissue emphasis image by emphasizing a first tissue of at least two radiation images of different energy bands based on a difference image generated by using a variable weight which is set based on a X-ray absorption coefficient ratio of a second tissue in two different energy bands; and
generating a plurality of images each corresponding to a plurality of frequency bands by performing frequency domain transform process and multi-scale decomposition process on the tissue emphasis image;
generating a plurality of first images by performing noise reduction process on the plurality of images each corresponding to the plurality of frequency bands;

generating a second image corresponding to the tissue emphasis image by combining the plurality of first images; and generating a diagnostic image by using at least one of the at least two radiation images of different energy bands and the second image.

2. The image processing method of claim 1, wherein the generating of the tissue emphasis image comprises:

generating the difference image by applying the variable weight to the at least two radiation images of different energy bands;

analyzing transform coefficients by transforming the difference image into a frequency domain;

repeatedly performing the generating of the difference image and the analyzing of the transform coefficients by changing the variable weight, and setting the variable weight corresponding to a point having a maximum change in a sum of high frequency coefficients of the difference image as an optimal weight; and outputting the difference image corresponding to the set optimal weight as the tissue emphasis image.

3. The image processing method of claim 1, further comprising correcting the at least two radiation images of different energy bands and generating the tissue emphasis image based on the corrected at least two radiation images.

4. The image processing method of claim 3, further comprising pre-processing the corrected at least two radiation images, and generating the diagnostic image based on the pre-processed at least two radiation images.

5. A non-transitory computer-readable medium, the medium storing a program that causes a computer including a processor to perform the method of claim 1.

6. An image processing apparatus comprising:

a tissue emphasis image generating unit configured to:

generate a tissue emphasis image by emphasizing a first tissue of at least two radiation images of different energy bands based on a difference image generated by using a variable weight which is set based on a X-ray absorption coefficient ratio of a second tissue in two different energy bands, generate a plurality of images each corresponding to a plurality of frequency bands by performing frequency domain transform process and multi-scale decomposition process on the tissue emphasis image, generate a plurality of first images by performing noise reduction process on the plurality of images each corresponding to the plurality of frequency bands, and generating a second image corresponding to the tissue emphasis image by combining the plurality of first images; and a combining unit configured to generate a diagnostic image by using at least one of the at least two radiation images of different energy bands and the second image.

7. The image processing apparatus of claim 6, wherein the tissue emphasis image generating unit is configured to:

generate the difference image by applying the variable weight to the at least two radiation images of different energy bands, analyze transform coefficients by transforming the difference image into a frequency domain, perform the generating of the difference image and the analyzing of the transform coefficients repeatedly by changing the variable weight, set the variable weight corresponding to a point having a maximum change in a sum of high frequency coefficients of the difference image corresponding to the changed variable weight as an optimal weight, and output the difference image corresponding to the set optimal weight as the tissue emphasis image.

8. The image processing apparatus of claim 6, further comprising a correcting unit configured to correct the at least two radiation images of different energy bands and to provide the corrected at least two radiation images to the tissue emphasis image generating unit.

9. The image processing apparatus of claim 6, further comprising a pre-processing unit configured to pre-process the corrected at least two radiation images, and to provide the pre-processed at least two radiation images to the tissue emphasis image generating unit.

10. A medical imaging apparatus comprising:

an image processing apparatus configured to generate a tissue emphasis image by emphasizing a predetermined tissue of at least two radiation images of different energy bands, to generate a plurality of images each corresponding to a plurality of frequency bands by performing frequency domain transform process and multi-scale decomposition process on the tissue emphasis image, to generate a plurality of first images by performing noise reduction process on the plurality of images each corresponding to the plurality of frequency bands, to generate a second image corresponding to the tissue emphasis image by combining the plurality of first images, and to generate a diagnostic image by combining at least one of the at least two radiation images of different energy bands and the second image.

11. The medical imaging apparatus of claim 10, further comprising a radiation image obtaining unit configured to irradiate radiation having at least two different energy bands onto a subject and to obtain the at least two radiation images of the subject.

12. The medical imaging apparatus of claim 10, further comprising a storage unit configured to store the generated diagnostic image and/or to store diagnosis information obtained from the generated diagnostic image in correspondence to the diagnostic image.

13. The medical imaging apparatus of claim 10, further comprising a communication unit configured to transmit the generated diagnostic image or transmitting diagnosis information obtained from the generated diagnostic image in correspondence to the diagnostic image.

14. An image processing apparatus comprising:

a tissue emphasis image generating unit configured to:

generate a tissue emphasis image in which a first tissue is emphasized based on a difference image generated by applying a variable weight to radiation images of different energy bands, generate a plurality of images each corresponding to a plurality of frequency bands by performing frequency domain transform process and multi-scale decomposition process on the tissue emphasis image, generate a plurality of first images by performing noise reduction process on the plurality of images each corresponding to the plurality of frequency bands, and generating a second image corresponding to the tissue emphasis image by combining the plurality of first images; and a combining unit configured to generate a diagnostic image in which a contrast of the first tissue other than second tissue is increased by using at least one of the radiation images of different energy bands and the second image.

15. The image processing apparatus of claim 14, wherein the variable weight is set based on a X-ray absorption coefficient ratio of the second tissue in two different energy bands.

16. The image processing apparatus of claim 15, wherein the tissue emphasis image generating unit is configured to:
  set an optimal weight based on a sum of high frequency coefficients of the difference image corresponding the set variable weight, when the variable weight is changed;
  generate the diagnostic image as the difference image corresponding to the optimal weight.

17. The image processing apparatus of claim 16, wherein the tissue emphasis image generating unit is configured to:
  set an optimal weight as the variable weight corresponding to a point having a maximum change in the sum of high frequency coefficients of the difference image.

* * * * *